United States Patent
Backus et al.

(10) Patent No.: US 11,589,170 B2
(45) Date of Patent: Feb. 21, 2023

(54) GENERALIZED METHOD FOR PROVIDING ONE OR MORE STIMULATION CODING PARAMETERS IN A HEARING AID SYSTEM FOR OBTAINING A PERCEIVABLE HEARING LOUDNESS

(71) Applicant: Oticon Medical A/S, Smørum (DK)

(72) Inventors: Bradford Backus, Vallauris (FR); Pierre Stahl, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 0 days.

(21) Appl. No.: 17/478,682

(22) Filed: Sep. 17, 2021

(65) Prior Publication Data
US 2022/0095059 A1    Mar. 24, 2022

(30) Foreign Application Priority Data

Sep. 18, 2020 (EP) .................................... 20196941

(51) Int. Cl.
*H04R 25/00* (2006.01)

(52) U.S. Cl.
CPC ........... *H04R 25/00* (2013.01); *H04R 25/353* (2013.01)

(58) Field of Classification Search
CPC . H04R 25/00; H04R 2225/49; H04R 2460/01
See application file for complete search history.

(56) References Cited

U.S. PATENT DOCUMENTS

| 6,115,478 A * | 9/2000 | Schneider ............ H04R 25/558 381/314 |
| 2007/0043403 A1 | 2/2007 | Blamey et al. |

(Continued)

*Primary Examiner* — Suhan Ni
(74) *Attorney, Agent, or Firm* — Birch, Stewart, Kolasch & Birch, LLP

(57) ABSTRACT

An aspect of the disclosure is to provide a method and a hearing aid system comprising; a microphone unit configured to receive an acoustical input and provide an audio signal based on the acoustical input, and wherein the audio signal includes a sound pressure level; a storing unit including a normal hearing loudness model, a loudness scheme, a stimulation model and a coding parameter model; a sound output unit configured to stimulate auditory nerve fibers of a recipient of the hearing aid system based on audible stimulations; a processing unit configured to; extract a normal hearing loudness based on the sound pressure level and the normal hearing loudness model, and the normal hearing loudness model includes a plurality of normal hearing loudness as a function of a plurality of sound pressure levels; transform the normal hearing loudness to a secondary hearing loudness according to a loudness scheme; determine a stimulation level within a dynamic range of a recipient of the hearing aid system based on the secondary hearing loudness and the stimulation model, where the stimulation model includes a relation between a plurality of stimulation levels and a plurality of secondary hearing loudness; determine one or more stimulation coding parameters based on the coding parameter model, where the coding parameter model includes a relation between the determined stimulation level and the one or more stimulation coding parameters; and wherein the processing unit is configured to generate the audible stimulations based on the determined one or more stimulation coding parameters and provide the audible stimulations via the sound output unit to the auditory nerve fibers of the recipient of the hearing aid system such that the recipient perceives the secondary hearing loudness.

20 Claims, 8 Drawing Sheets

(56) References Cited

U.S. PATENT DOCUMENTS

2013/0103396 A1* 4/2013 Swanson ............. G10L 21/0316
  704/E19.039
2015/0264482 A1* 9/2015 Neely ...................... H04R 1/10
  381/320
2016/0199643 A1 7/2016 Segovia Martinez

* cited by examiner

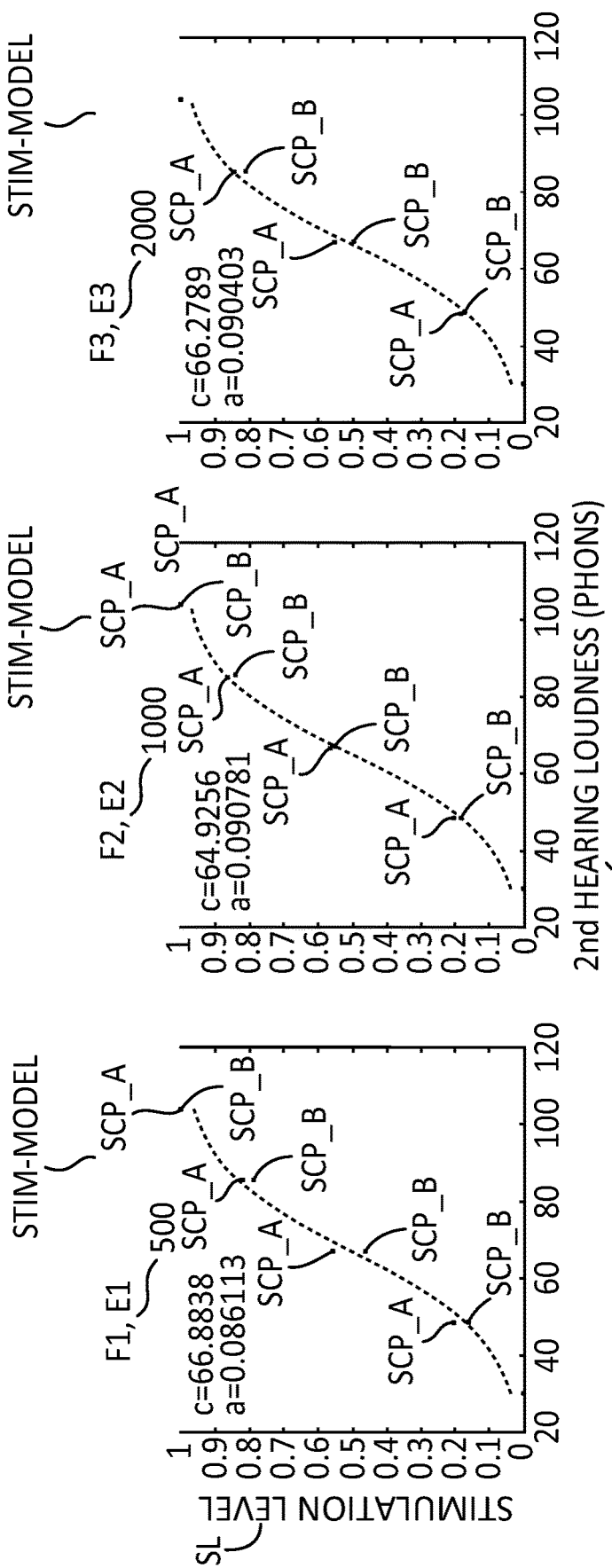

GENERALIZED METHOD FOR PROVIDING ONE OR MORE STIMULATION CODING PARAMETERS IN A HEARING AID SYSTEM FOR OBTAINING A PERCEIVABLE HEARING LOUDNESS

FIELD

The present disclosure relates to a generalized method for providing one or more stimulation coding parameters in a hearing aid system for obtaining a perceivable hearing loudness.

BACKGROUND

A hearing aid that system is adapted to improve or augment the hearing capability of a recipient by receiving an acoustic signal from a recipient's surroundings, generating a corresponding audio signal, possibly modifying the audio signal and providing the possibly modified audible signal as an audible signal to at least one of the recipient's ears or auditory nerve fibers of the recipient's cochlea. Such audible signals may be provided in the form of an acoustic stimulation transferred to the recipient's ear via a speaker, or provided in the form of an electrical stimulation transferred to the recipient's auditory nerve fibers via an electrode array, or provided in the form of a mechanical stimulation transferred to the recipient via a vibrator transferring the mechanical stimulation in the form of vibrations into the skull of the recipient.

The different types of hearing aid systems may be used together in any combinations, and each of them are fitted differently resulting in different perceived hearing loudness provided by the stimulation applied to the recipient's ear or cochlea. The recipient will perceive different loudness on both ears which unfortunately results in acoustical discomfort when receiving stimulation on both ears.

SUMMARY

An aspect of the disclosure is to provide a method for providing one or more stimulation coding parameters which can be used for any types of hearing aid system allowing a unified and consistent fitting and coding across devices and which can resulting in an aligned hearing loudness between different types of hearing aid system worn by the recipient.

A further aspect of the disclosure is to provide a method which reduces the auditory discomfort for the recipient wearing different types of hearing aid systems.

An even further aspect of the disclosure is to provide a method for which the determination of the one or more stimulation coding parameters to obtain a secondary hearing loudness is done faster, resulting in that the method is suitable to be executed in a processing unit of a hearing aid system during the use of the hearing aid system and continuously.

The aspect of the disclosure is achieved by a method for providing one or more stimulation coding parameters in a hearing aid system for obtaining a perceivable secondary hearing loudness. The hearing aid system may be an acoustical hearing aid configured to provide an acoustical stimulation via a speaker, or a cochlea implant system configured to provide an electrical stimulation via an electrode array, or a vibrator hearing aid configured to provide a mechanical stimulation via a vibrator.

The method further comprises receiving an acoustical input and providing an audio signal based on the acoustical input, and wherein the audio signal includes a sound pressure level at a frequency within a frequency range of between 10 Hz and 12 KHz. The sound pressure level may be across frequencies bandlimited to a frequency range. A normal hearing loudness may be determined based on the sound pressure level and a normal hearing loudness model, where the normal hearing loudness model includes a plurality of normal hearing loudness as a function of a plurality of sound pressure levels and for one or more frequencies. The normal hearing loudness may be determined by the normal hearing loudness model by extracting the normal hearing loudness from the model at the sound pressure level and the frequency of the audio signal. The normal hearing loudness may be transformed to a secondary hearing loudness according to a loudness scheme, and where the loudness scheme includes a relation between a plurality of normal hearing loudness and a plurality of secondary hearing loudness. The transformation may include compression and/or expansion of the normal hearing loudness. Then, a stimulation level at the frequency may be determined within a dynamic range of a recipient of the hearing aid system based on the secondary hearing loudness and a stimulation model, and where the dynamic range defines a ratio between the largest (a hearing comfortable level) and smallest loudness (a hearing threshold) which a recipient can perceive. The stimulation model may include a relation between a plurality of stimulation levels and a plurality of secondary hearing loudness. Furthermore, one or more stimulation coding parameters may be determined at the frequency and based on a coding parameter model, where the coding parameter model includes a relation between the determined stimulation level and the one or more stimulation coding parameters for one or more frequencies. The method further comprises generating audible stimulations based on the one or more stimulation coding parameters and providing the audible stimulations via a sound output unit of the hearing aid system to auditory nerve fibers of the recipient of the hearing aid system such that the recipient perceives the secondary hearing loudness.

By performing the transformation from the normal hearing loudness to the secondary hearing loudness results in a hearing aid system will provide a loudness growth that will be comparable to a loudness growth of a normal ear having no or minimal hearing loss. In an example where the recipient wears the hearing aid system on one ear and nothing on the opposite ear, the behavior of loudness on both ears will be similar resulting in an improved hearing experience.

A further aspect of the disclosure is achieved by a hearing aid system comprising a microphone unit that may be configured to receive an acoustical input and provide an audio signal based on the acoustical input, and wherein the audio signal includes a sound pressure level. The system further comprises a storing unit that includes a normal hearing loudness model, a loudness scheme, a stimulation model and a coding parameter model, and the system includes a sound output unit configured to stimulate auditory nerve fibers of a recipient of the hearing aid system, and a processing unit configured to extract a normal hearing loudness based on the sound pressure level and the normal hearing loudness model. The normal hearing loudness model includes a plurality of normal hearing loudness as a function of a plurality of sound pressure levels. Furthermore, the processing unit may be configured to transform the normal hearing loudness to a secondary hearing loudness according to the loudness scheme; determine a stimulation level within a dynamic range of a recipient of the hearing aid system based on the secondary hearing loudness and the stimulation model, where the stimulation model includes a relation between a plurality of stimulation levels and a plurality of secondary hearing loudness. The processing unit may be configured to determine one or more stimulation coding parameters based on the coding parameter model, where the coding parameter model includes a relation between the determined stimulation level and the one or more stimulation coding parameters. Furthermore, the processing unit may be configured to generate audible stimulations based on the determined one or more stimulation coding parameters and provide the audible stimulation via the sound output unit to the auditory nerve fibers of the recipient of the hearing aid system such that the recipient perceives the secondary hearing loudness.

The normal hearing loudness model may be determined based on one or more normal hearing loudness as a function of a plurality of sound pressure levels of one or more normal hearing persons. The sound pressure level may be applied The normal hearing loudness model may be determined for a frequency range between 10 Hz and 12 KHz.

The normal hearing loudness model may be determined for a frequency range including audible frequencies.

The hearing aid system may be an acoustical hearing aid where the audible stimulations are provided as an acoustical stimulation via the sound output unit being a speaker. The hearing aid system may be a cochlear implant system where the audible stimulations are provided as an electrical stimulation via the sound output unit being an electrode array implanted into a cochlea of the recipient. The hearing aid system may be a vibrator hearing aid where the audible stimulations are provided as a mechanical stimulation via the sound output unit being a vibrator.

The acoustical hearing aid being a Behind-The-Ear hearing aid, an In-The-Ear hearing aid, an In-The-Canal hearing aid, or a Completely-In-Canal hearing aid. The vibrator hearing aid may be coupled to the skull of the recipient via a fixture and an abutment where the mechanical stimulation, including the audio signal, is transferred from the vibrator hearing and via the fixture and the abutment onto the skull of the recipient. In another example, the vibrator hearing aid includes an external part and an implantable part or only an implantable part. The vibrator may be arranged within the implantable part, and the implantable part is arranged on or at the head of the recipient and between an outer skin layer and the skull of the recipient. The external part may be arranged at or on the head of the recipient via a magnetic interface to the implantable part. In this example, both parts include a magnet which attract and keep the external part at or on the head of the recipient.

The cochlear implant system may include an external part and an implantable part or only an implantable part. The electrode array may be implanted and connected to the implantable part.

The microphone unit may include one or more microphones configured to receive the acoustical input. The storing unit may be a memory unit, such as a Read Only Memory (ROM) or a Random Access Memory (RAM).

The sound output unit may a speaker, a vibrator or an electrode array.

The processing unit may be arranged in the external part and/or the implantable part The normal hearing loudness model may include a plurality of normal hearing loudness as a function of a plurality of sound pressure levels for a specific frequency range. The normal hearing loudness is defined as a loudness perceived by a normal hearing person relative to a sound pressure level of an audio input. The normal hearing loudness model may be determined based on a plurality of normal hearing people. The normal hearing loudness model may be based on a standard, such as The International Organization for Standardization (ISO) 226 for sound level to loudness of normal hearing.

The hearing impaired may do better than normal hearing people in intensity discrimination, because the loudness growth functions for the hearing impaired are faster than for the normal hearing people. The loudness scheme is used for transforming the normal hearing loudness to the secondary hearing loudness for a specific frequency range, where the secondary hearing loudness corresponds to a loudness perceived by a hearing impaired. The loudness scheme may include a relation between a plurality of normal hearing loudness perceived by normal-hearing persons and a plurality of secondary hearing loudness perceived by hearing impaired people of a specific frequency range. The difference in the loudness growth function between normal hearing people and hearing impaired people may be include into the loudness scheme by adding expansion and/or compression, i.e. changing the slope of the relation for a specific frequency range. By changing the slope of the relation, it is possible to adjust the intensity discrimination to do better or worse than a normal hearing person for a particular loudness range. Thus, it is possible to align the intensity discrimination between different hearing aid systems, and thereby, it is possible for the hearing impaired to obtain equally or nearly equally intensity discrimination on both ears even if the recipient is using different hearing aid systems on both ears.

For a specific frequency range and within the dynamic range of the recipient of the specific frequency range, a loudness growth function may be fitted to the recipient that includes the level of gain applied to different sound pressure levels of the audio signal resulting in a level of the audible stimulations. The loudness growth function may include an incremental gain that is larger between a hearing threshold level and an intermediate knee point than the incremental gain between the intermediate knee point and a hearing comfortable level.

The incremental gain defined by the loudness growth function may be applied to the loudness scheme such that the relation between the plurality of normal hearing loudness and the plurality of secondary hearing loudness corresponds to the incremental gain of the loudness growth function.

The loudness scheme may include a first relation between a plurality of normal hearing loudness perceived by a normal hearing person and a plurality of secondary hearing loudness perceived by a hearing impaired, where the first relation is equate resulting in a primary slope, and/or, the loudness scheme may include a second relation between a plurality of normal hearing loudness perceived by a normal hearing person and a plurality of secondary hearing loudness perceived by a hearing impaired, where the second relation includes a secondary first slope and a secondary second slope, and where the secondary first slope is larger than the secondary second slope.

The relation defines a gain applied to the normal hearing loudness resulting in the secondary hearing loudness, and the slope may define the incremental gain. The secondary first slope may be larger than the primary slope, and the secondary second slope may be smaller than the primary slope. That means, the incremental gain defined by the secondary first slope is larger than the incremental gain defined by the primary slope. Furthermore, the incremental gain of the secondary second slope is smaller than the incremental gain of the primary slope.

The relation, i.e. the first relation and the second relation, may be dynamically determined based on a selection of a hearing aid program storied into the storing unit. A hearing aid program may determine the settings of the hearing aid, such as acoustical settings, fitting settings, software settings and/or firmware settings. The selection of hearing aid programs may be determined by an acoustical environment of the recipient.

The first relation in the loudness scheme may be determined based on International Organization for Standardization number 226 (ISO-226), and/or, the second relation in the loudness scheme may be determined based on a fitting of the first relation which includes changing the primary slope differently within multiple ranges of the plurality of the normal hearing loudness or of the plurality of the secondary hearing loudness.

The secondary hearing loudness may be a loudness perceived by one or more recipients of cochlear implant systems, bone conduction hearing aids or acoustical hearing aids not being cochlear implant systems or bone conduction hearing aids.

The stimulation model may include a relation between the plurality of stimulation levels and the plurality of secondary hearing loudness of other recipients or of the recipient of the hearing aid system. The relation may be determined by a sigmoid function.

The stimulation model may be determined based on following equation:

$$SL = \frac{1}{1 + e^{-a(2HL-c)}},$$

where SL is the stimulation level, '2HL' is the secondary hearing loudness, a and c are fitting parameters. The fitting parameters may be determined based on a sigmoid function fitting of a relation between a plurality of stimulation levels and a plurality of secondary hearing loudness of multiple other recipients or of the recipient. By being able to apply a sigmoid function to the relation between stimulation level and the secondary hearing loudness results in a faster way of determining the one or more stimulation coding parameters needed for generating the audible stimulations.

The one or more stimulation coding parameters may include at least pulse duration, pulse current amplitude, pulse charge delivered, pulse or a sequence of pulses energy defined over an integration time window, or applied gain level to an acoustical input resulting in an amplified sound pressure level.

The stimulation model is useable for determining the one or more stimulation coding parameters, as it has been shown that the relation between the plurality of stimulation levels and the plurality of secondary hearing loudness can be usefully defined by a Sigmoid function no matter which type of coding parameter has been used. For example, the relation when using pulse duration and the relation when using pulse current amplitude are both definable by a Sigmoid function. Since the Sigmoid function is useable for different types of coding parameters it is then possible to determine a generalized method for providing one or more stimulation coding parameters for different type of hearing aid systems. Although other functions can be used, the advantage of the Sigmoid is that it fits the data well and is smooth, thus avoiding region transition artifacts that piecewise functions would have.

The level of stimulation may be determined by the one or more stimulation coding parameters, and where the level of stimulation may be determined by following equation:

$$SL = \frac{\log(SCP) - \log(X_T)}{\log(X_C) - \log(X_T)}$$

Where SL is the stimulation level, where SL is stimulation level, SCP is the coding quantity that could be made of one or more stimulation parameters, $X_T$ is a first coding parameter threshold at a hearing threshold level (T-level) predetermined for the recipient, $X_C$ is a second coding parameter threshold at a hearing comfortable level (C-level) predetermined for the recipient, and where x, $X_T$, and $X_C$ are the same coding parameter type. As the stimulation level is determined by the stimulation model it is then possible to determined one of the one or more stimulation coding parameters, SCP, by the coding parameter model expressed by this equation:

$$SCP = e^{\left(SL \cdot \log\left(\frac{X_C}{X_T}\right) + \log(X_T)\right)}$$

The acoustical input may be divided into a plurality of audio signals via a filter bank, and wherein the audio signal of the plurality of audio signals is band limited to a frequency range determined by a bandwidth and a center frequency of a bandpass filter of the filter bank.

The method for providing one or more stimulation coding parameters applies to each of the plurality of audio signals, and therefore, the processing unit is configured to perform the method for each of the plurality of audio signals in parallel.

Instead of selecting a single stimulation coding parameter, such as pulse duration or pulse current amplitude, to fit and code secondary hearing loudness, it is of advantage to combine the one or more stimulation coding parameters which correlates optimally to the secondary hearing loudness. By combining for example pulse duration and pulse current amplitude and pulse rate which allows higher resolution loudness control than changing one single stimulation coding parameter alone due to technical limitations of the hardware in the hearing aid system. Furthermore, the combination of multiple stimulation coding parameters enables using different stimulation rates to control pitch while retaining a desired loudness perception, and furthermore, it enables the possibility of changing the shape of stimulation pulses when the hearing aid system is a cochlear implant system.

A method for combining two or more stimulation coding parameters may include determining a relation between secondary hearing loudness and two or more stimulation coding parameters for other recipients of hearing aid systems or of the recipient of the hearing aid system. The secondary hearing loudness may not go below the hearing threshold level (T-level) or above the comfortable hearing threshold level (C-level), and therefore, it is a need that the relation is fitted to the recipient's T-level and C-level. As the relation is fitted to the recipient, the two or more stimulation coding parameters are then used for generating audible stimulations, e.g. electrical stimulation.

The determining of the relation may be done through experiments of recipients of hearing aid systems or of the recipient of the hearing aid system, where the recipient is asked to maintain an equal loudness percept while allowing to trade the various stimulation coding parameters off against each other, e.g. trading off electrode current and stimulation rate when the hearing aid system(s) is a cochlear implant system. This is repeated at multiple loudness levels, i.e. from the T-level to the C-level. The two or more stimulation coding parameters are used for providing audible stimulations to the recipient which then perceives the audible stimulations as loudness.

The method for determining the relation provides both the sensitivity of loudness to each of the electrode of the electrode array as well as the relation between the two or more stimulation coding parameters.

The relation may be determined by a relation between the energy of the audible stimulations provided by a stimulation coding parameter and the perceived loudness of the recipient. By determine the relation in energy results in a closer correlation between the different relations of the different type of stimulation coding parameters and loudness, and therefore, it is of an advantage to determine the relation in energy as an improved correlation is obtained between the two or more stimulation coding parameters.

For a cochlear implant system, the energy of the audible stimulations may be approximated by following equation:

$$E = R(e) \cdot \int_t^T I(t)^2 dt$$

where $R(e)$ represents a resistive load of the auditory nerve fibers on the electrode when they are converting the current into action potentials. In this example, it is assumed to be a slowly varying parameter with time. Although, it is assumed to depends on the electrode properties grounding and the biological surrounding of the electrode, such as neural health. It is assumed to not to be dependent on the changing of the type of stimulation coding parameters. T is an integration window duration that is set to a time that makes it possible to code the loudness precepts by the recipient needed to capture the modulation rates of speech in the audible stimulations. The integration window may be set to 8 milliseconds. Introducing T, allows for variable stimulation rates of the audible stimulations without changing the percept of secondary hearing loudness. The shape of the integration window may be square or a non-square window function of t, w(t). 'I' represents the electrode current. In this example, the exponent is a square which represents an integral quantity that is proportional to energy. The exponent may be somewhat higher or lower or may depend on the resistive load, $R(e)$.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIGS. 6A to 6C illustrate a stimulation model, and

DETAILED DESCRIPTION

Figure 1C:
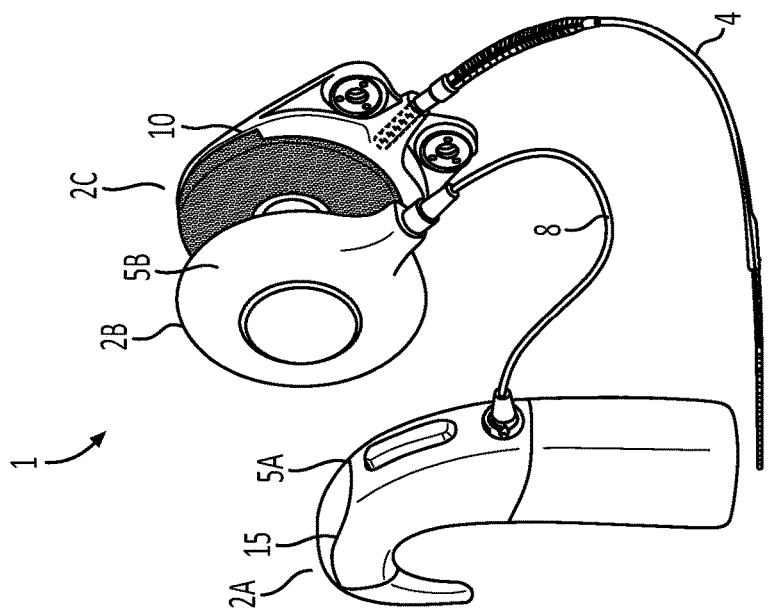
FIGS. 1A to 1C illustrate different example of a hearing aid system.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, etc. (collectively referred to as "elements"). Depending upon particular application, design constraints or other reasons, these elements may be implemented using other equivalent elements.

The hearing aid that is adapted to improve or augment the hearing capability of a recipient by receiving an acoustic signal from a recipient's surroundings, generating a corresponding audio signal, possibly modifying the audio signal and providing the possibly modified audio signal as an audible signal to at least one of the recipient's ears. Such audible signals may also be provided in the form of an acoustic signal transferred as mechanical vibrations to the recipient's inner ears through bone structure of the recipient's head.

The hearing aid is adapted to be worn in any known way. This may include arranging a unit of the hearing aid attached to a fixture implanted into the skull bone such as in a Bone Anchored Hearing Aid or at least a part of the hearing aid may be an implanted part.

A "hearing system" or a "cochlear implant system" refers to a system comprising one or two hearing aids, one or two cochlear implants, and a "binaural hearing system" refers to a system comprising two hearing aids or two cochlear implants where the devices are adapted to cooperatively provide audible signals to both of the recipient's ears or the hearing aid of bone conduction type or an acoustical hearing aid may be part of a bimodal system comprising a cochlear implant and a hearing aid or a bone conduction hearing aid. The system may further include an external device(s) that communicates with at least one hearing aid, the external device affecting the operation of the hearing aids and/or benefitting from the functioning of the hearing aids. A wired or wireless communication link between the at least one hearing aid and the external device is established that allows for exchanging information (e.g. control and status signals, possibly audio signals) between the at least one hearing aid and the external device. Such external devices may include at least one of remote controls, remote microphones, audio gateway devices, mobile phones, public-address systems, car audio systems or music players or a combination thereof. The audio gateway is adapted to receive a multitude of audio signals such as from an entertainment device like a TV or a music player, a telephone apparatus like a mobile telephone or a computer, a PC. The audio gateway is further adapted to select and/or combine an appropriate one of the received audio signals (or combination of signals) for transmission to the at least one hearing aid. The remote control is adapted to control functionality and operation of the at least one hearing aids. The function of the remote control may be implemented in a SmartPhone or other electronic device, the SmartPhone/electronic device possibly running an application that controls functionality of the at least one hearing aid.

In general, a hearing aid or a cochlear implant includes i) an input unit such as a microphone for receiving an acoustic signal from a recipient's surroundings and providing a corresponding input audio signal, and/or ii) a receiving unit for electronically receiving an input audio signal. The hearing aid further includes a signal processing unit for processing the input audio signal and an output unit for providing an audible signal to the recipient in dependence on the processed audio signal.

The input unit may include multiple input microphones, e.g. for providing direction-dependent audio signal processing. Such directional microphone system is adapted to enhance a target acoustic source among a multitude of acoustic sources in the recipient's environment. In one aspect, the directional system is adapted to detect (such as adaptively detect) from which direction a particular part of the microphone signal originates. This may be achieved by using conventionally known methods. The signal processing unit may include amplifier that is adapted to apply a frequency dependent gain to the input audio signal. The signal processing unit may further be adapted to provide other relevant functionality such as compression, noise reduction, etc. The output unit may include an output transducer for providing mechanical vibrations either transcutaneously or percutaneously to the skull bone.

Figure 1A:
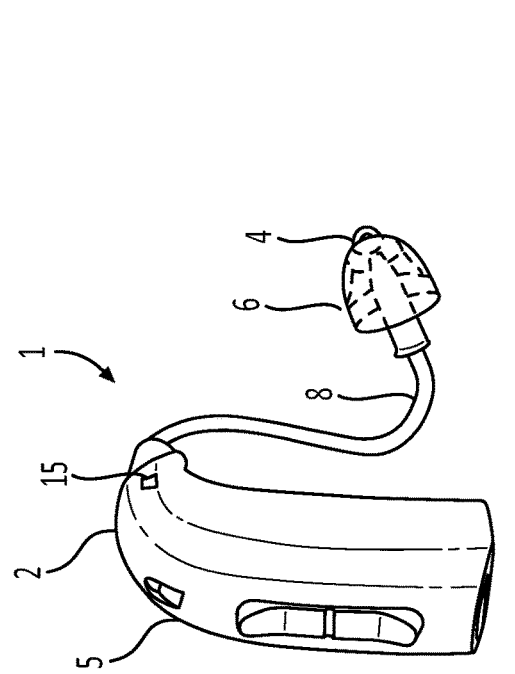
Figure 1B:
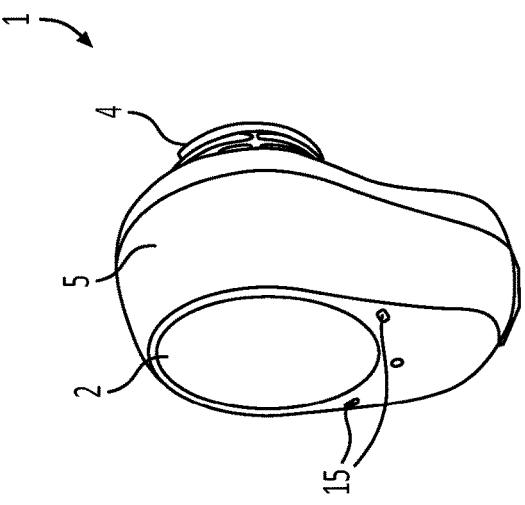

FIGS. 1A to 1C illustrate different examples of a hearing aid system 1. FIG. 1A illustrates an example of an acoustical hearing aid being a Behind-The-Ear hearing aid. In this example, a microphone unit 15 is arranged in a housing 5 configured to be placed on and behind the ear, and within the housing 5 the processing unit 2 is arranged. The housing 5 is connected to an in-the-ear unit 6 via a connection part 8. A sound output unit 4 is arranged within the in-the-ear unit 6. The sound output unit is a speaker configured to provide audible stimulations based on the audio signal, and where the audible stimulations include acoustical waves.

The microphone unit 15 may include one or more microphones, wherein each of the microphones is configured to receive an acoustical input and provide an audio signal based on the acoustical input.

FIG. 1B illustrates an example of a bone conduction hearing aid being a percutaneous bone conduction hearing aid. In this example, a microphone unit 15 is arranged in a housing 5 configured to be placed on the head, and within the housing 5 the processing unit 2 is arranged. A sound output unit 4 is arranged within the housing 5. The sound output unit 4 is a vibrator configured to apply acoustical vibrations onto the skull of the recipient via an abutment (not shown) which is in contact with the skull.

FIG. 1C illustrates an example of a cochlear implant system 1 which in this example includes a first external unit 5A and a second external unit 5B that are connected via a connection part 8. An implantable unit 10 is arranged between the skin and skull of the recipient, and where the implantable unit 10 is transcutaneously linked to the second external unit 5B. In this example the sound output unit 4 is connected to the implantable unit 10, and the sound output unit 4 is an electrode array including a plurality of electrodes, where each of the electrodes is configured to provide an electrical stimulation to auditory nerve fibers of the cochlear of the recipient for enhancing the recipient's hearing capability. The sound processing unit (2A,2B,2C) may be arranged within any of the external units (2A and 2B) and/or in the implantable unit (2C). In other examples, the cochlear implant system 1 may be a fully implantable cochlear implant system.

Figure 2A:
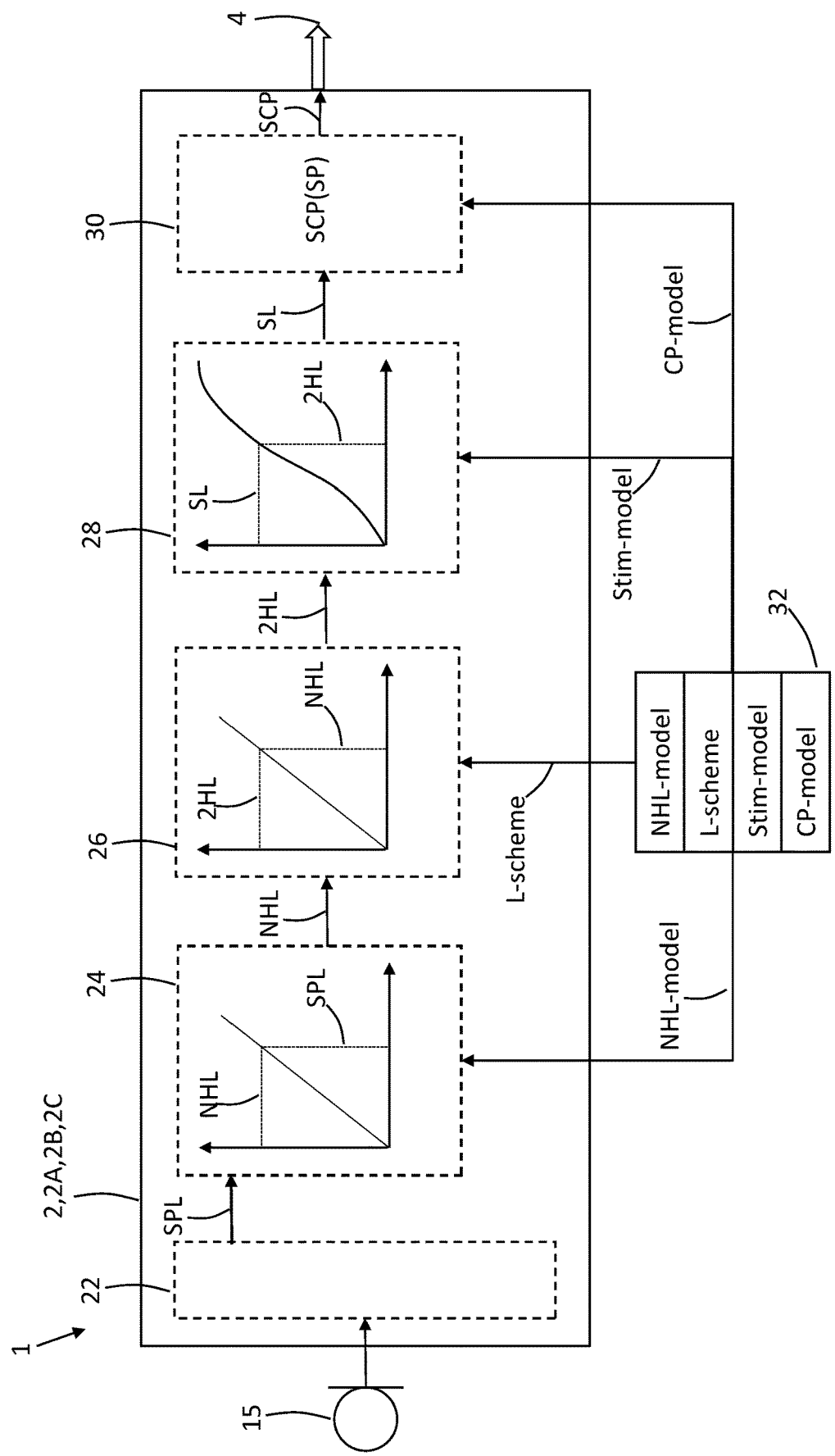
FIGS. 2A to 2C illustrate different example of a hearing aid system.
Figure 2B:
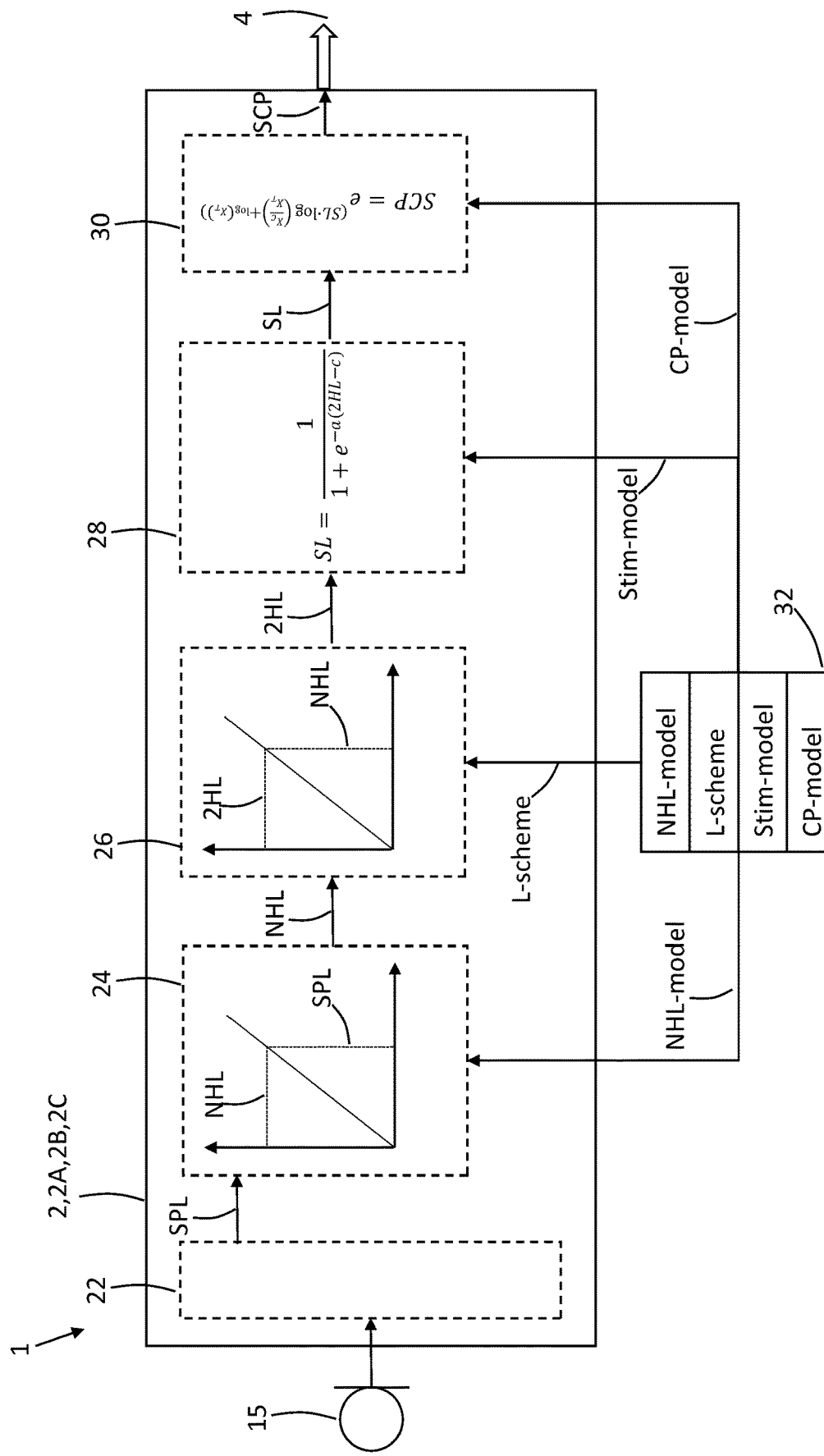
Figure 2C:
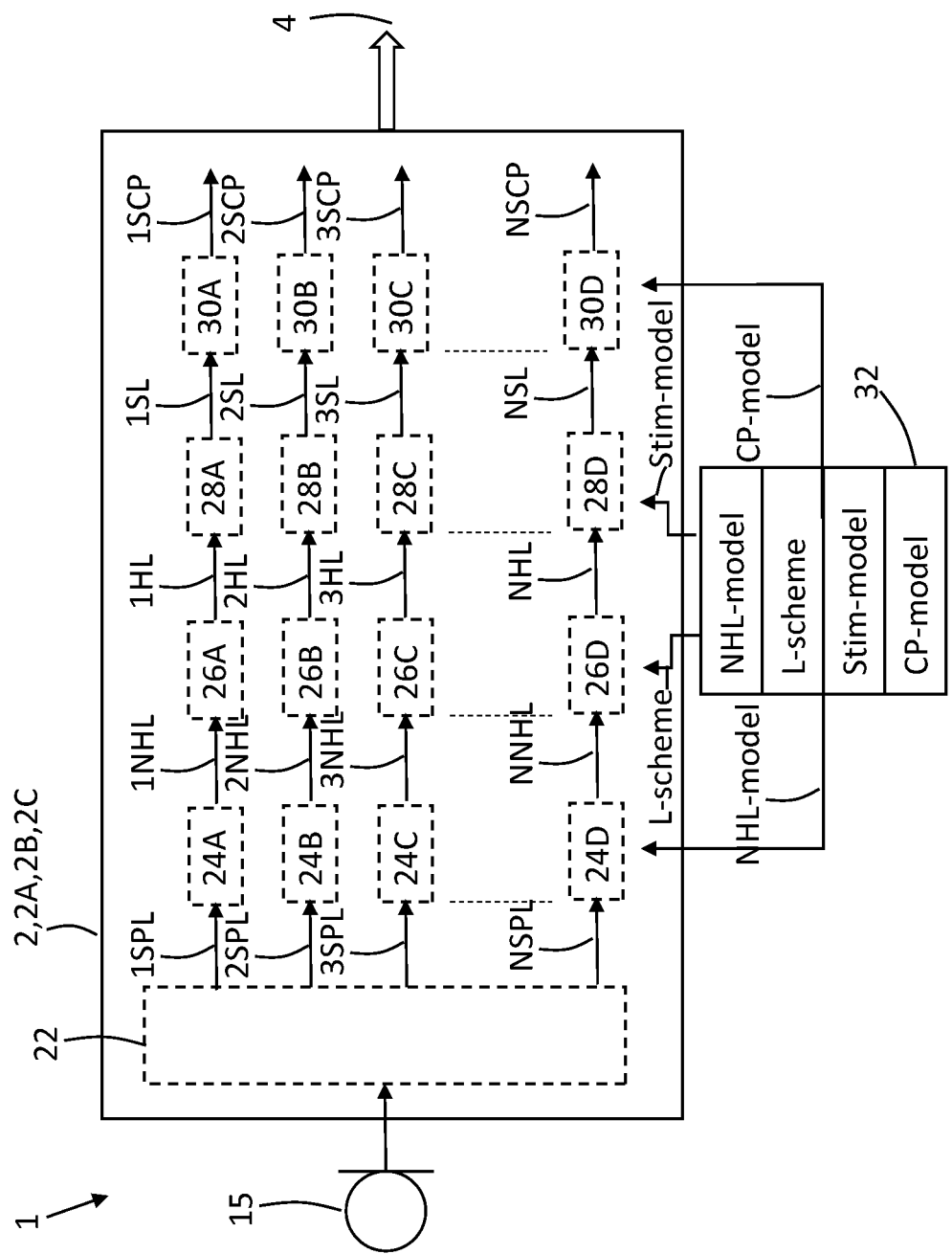

FIGS. 2A to 2C illustrate an example of the hearing aid system 1 including the processing unit (2, 2A,2B,2C), the microphone unit 15, the sound output unit 4 and a storing unit 32. The processing unit (2, 2A,2B,2C) is configured to retrieve what is being storied on the storing unit 32. In this example, the acoustical input is received by the microphone unit 15 and converted 22 into an audio signal with a sound pressure level SPL and at a frequency within a specific frequency range. A normal hearing loudness is extracted or determined 24 for the frequency based on the sound pressure level SPL and a normal hearing loudness model (NHL-model). The normal hearing loudness model (NHL-model) is stored within the storing unit 32. The processing unit (2,2A,2B,2C) may be configured to retrieve the normal hearing loudness model when the microphone unit 15 receives an acoustical input, when the hearing aid system 1 is turned on or during initiation of the hearing aid system 1. The normal hearing loudness NHL is then transformed 26 to a secondary hearing loudness 2HL at the frequency based on a loudness scheme (L-scheme) stored in the storing unit 32. The loudness scheme (L-scheme) may be defined by an equation or include a relation between a plurality of normal hearing loudness perceived by a normal-hearing person and a plurality of secondary hearing loudness perceived by a hearing-impaired person. The loudness scheme (L-scheme) is retrieved by the processing unit (2,2A,2B,C). The secondary hearing loudness 2HL should then be converted to audible stimulations which can be perceived by the recipient. A stimulation level SL is then determined 28 at the frequency and within a dynamic range of the recipient of the hearing aid system 1, where the stimulation level SL is determined based on the secondary hearing loudness 2HL and a stimulation model (Stim-model). The dynamic range defines the range of loudness which implies loudness just audible for the recipient to loudness which is just below a level of loudness which is uncomfortable for the recipient to perceive. Therefore, it is very important that the stimulation level SL is within the dynamic range otherwise the recipient will experience either uncomfortable audible stimulations or no perceivable audible stimulations.

The determined stimulation level SL is then used for determining 30 one or more stimulation coding parameters SCP at the frequency and based a coding parameter model (CP-model) which determines the relation between the stimulation level and the one or more stimulation coding parameters SCP. The processing unit (2,2A,2B,2C) is then configured to generate the audible stimulations based on the determined one or more stimulation coding parameters SCP and provide the audible stimulations via the sound output unit 4 to the auditory nerve fibers of the recipient of the hearing aid system such that the recipient perceives the secondary hearing loudness.

FIG. 2B illustrates a similar example as in FIG. 2A, but in this specific example the stimulation level SL is determined 28 within the dynamic range of the recipient of the hearing aid system 1, and where the stimulation level SL is determined based on the secondary hearing loudness 2HL and the stimulation model (Stim-model) which is defined by the equation $$SL = \frac{1}{1 + e^{-a(2HL-c)}},$$

where SL is the stimulation level, 2HL is a secondary hearing loudness, a and c are fitting parameters which is determined based on a frequency of the audio signal.

For generating the audible stimulations, the determined stimulation level SL is then used for determining 30 one or more stimulation coding parameters SCP via the coding parameter model (CP-model) which in this specific example includes following equation:

$$SCP = e^{\left(SL \cdot \log\left(\frac{X_C}{X_T}\right) + \log(X_T)\right)},$$

where SL is the stimulation level, SCP is one of the one or more stimulation coding parameters, $X_T$ is a first coding parameter threshold at a hearing threshold level (T-level) predetermined for the recipient, $X_C$ is a second coding parameter threshold at a hearing comfortable level (C-level) predetermined for the recipient, and where SCP, $X_T$, and $X_C$ are the same coding parameter type.

The processing unit (2,2A,2B,2C) is then configured to generate the audible stimulations based on the determined one or more stimulation coding parameters SCP and provide the audible stimulations via the sound output unit 4 to the auditory nerve fibers of the recipient of the hearing aid system such that the recipient perceives the secondary hearing loudness.

FIG. 2C illustrates a similar example as depicted in FIGS. 2A and 2B, but in this specific example the acoustical input is divided 22 into a plurality of audio signals (1SPL–NSPL) via a filter bank, and wherein the audio signal of the plurality of audio signals is band limited to a frequency range determined by a bandwidth and a centre frequency of a bandpass filter of the filter bank. Furthermore, for each of the audio signal (1SPL–NSPL) one or more stimulation coding parameters (1SCP–NSCP) are determined by the processing unit (2, 2A, 2B, 2C), and audible stimulations are generated for each of the audio signal (1SPL–NSPL) and transferred to the sound output unit 4.

Figure 3:
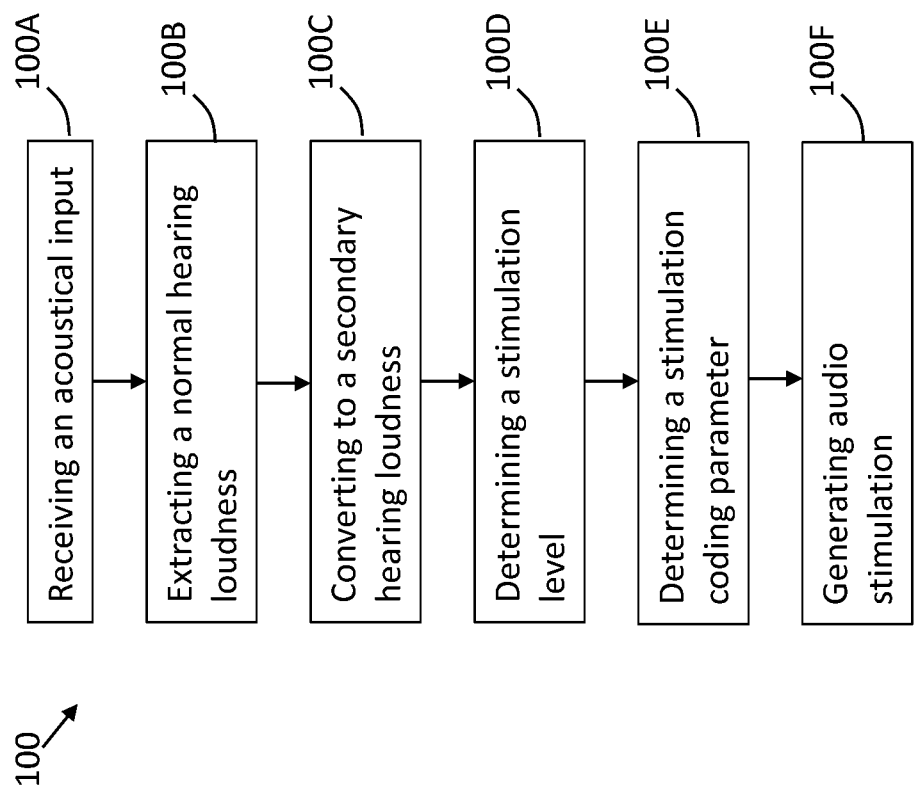
FIG. 3 illustrates a method.

FIG. 3 illustrates a method 100 for providing one or more stimulation coding parameters (SCP) in a hearing aid system 1 for obtaining a perceivable secondary hearing loudness, comprising;
  receiving 100A an acoustical input and providing an audio signal based on the acoustical input, and wherein the audio signal includes a sound pressure level;
  extracting 100B a normal hearing loudness based on the sound pressure level and a normal hearing loudness model, where the normal hearing loudness model includes a plurality of normal hearing loudness as a function of a plurality of sound pressure levels;
  transforming 100C the normal hearing loudness to a secondary hearing loudness according to a loudness scheme;
  determining 100D a stimulation level within a dynamic range of a recipient of the hearing aid system based on the secondary hearing loudness and a stimulation model, where the stimulation model includes a relation between a plurality of stimulation levels and a plurality of secondary hearing loudness;
  determining 100E one or more stimulation coding parameters based on a coding parameter model, where the coding parameter model includes a relation between the determined stimulation level and the one or more stimulation coding parameters; and
  generating 100F audible stimulations based on the one or more stimulation coding parameters and provide the audible stimulations via a sound output unit of the hearing aid system to auditory nerve fibers of the recipient of the hearing aid system such that the recipient perceives the secondary hearing loudness.

Figures 4, 5:
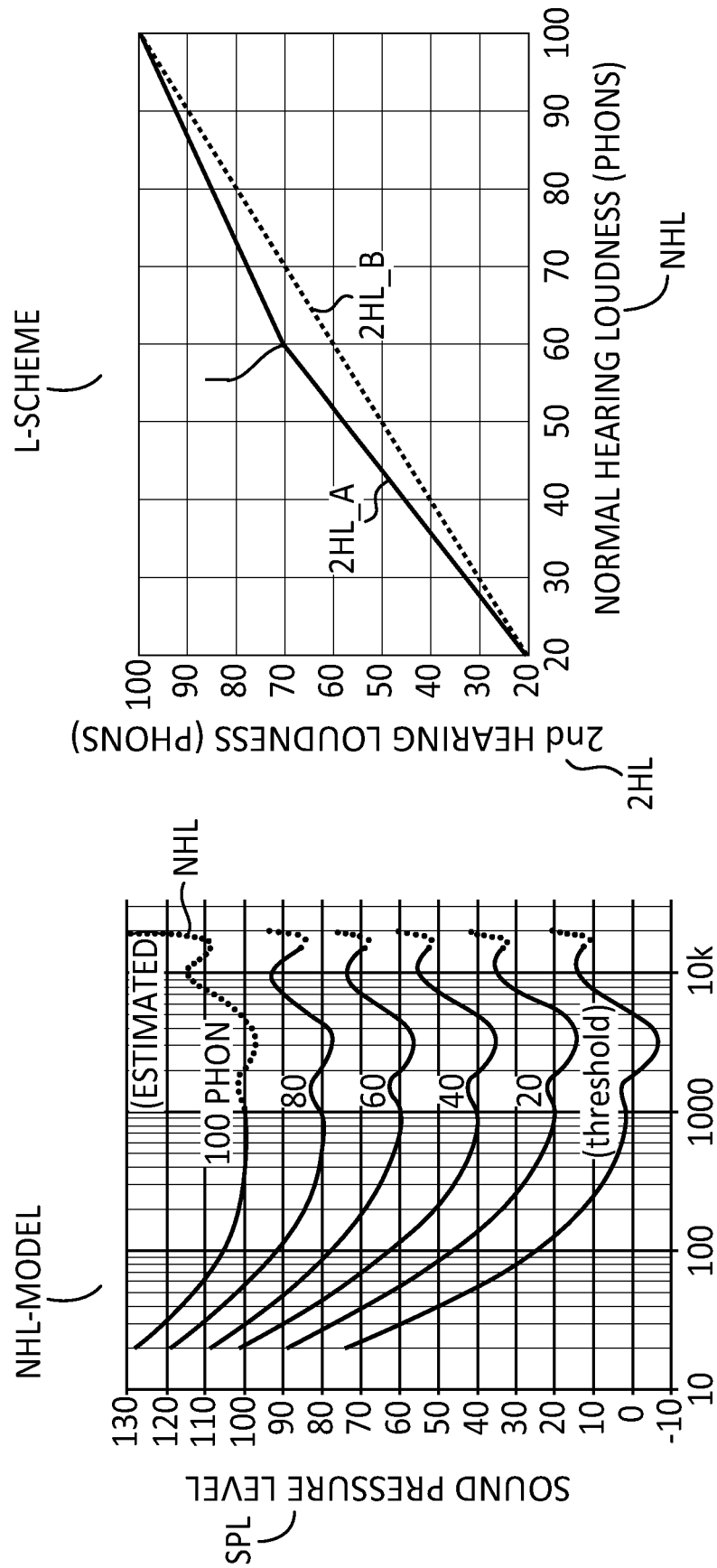
FIG. 4 illustrates an example of the normal hearing loudness model.
FIG. 5 illustrates an example of the loudness scheme.

FIG. 4 illustrates an example of the normal hearing loudness model (NHL-model) for different frequencies. Via the model it is possible to extract or determine a normal hearing loudness based on the sound pressure level of the audio signal and for a specific frequency range.

FIG. 5 illustrates an example of the loudness scheme where the normal hearing loudness NHL is transformed into the secondary hearing loudness 2HL. The figure illustrates two examples of transformation, where the first example includes a transformation to the secondary hearing loudness 2HL_A with different incremental gain above and below a kneepoint (I). In the second example, the transformation to the secondary hearing loudness 2HL_B is 1:1, i.e. the relation is equity.

FIGS. 6A to 6C illustrate a stimulation model including relation between a plurality of stimulation levels SL and a plurality of secondary hearing loudness 2HL for a frequency (F1,F2,F4) or for an electrode (E1, E2, E3) of the sound output unit 4 and for different stimulation coding parameters (SCP_A, SCP_B). It is seen that for different stimulation coding parameters the relation can be approximated or determined by a Sigmoid function. An example of a Sigmoid function:

$$SL = \frac{1}{1 + e^{-a(2HL-c)}},$$

where SL is the stimulation level, 2HL is the secondary hearing loudness, a and c are fitting parameters. The fitting parameters varies slightly between the FIGS. 6A, 6B, and 6C, and therefore, it can be approximated that the fitting parameters are independent of the frequency and type of stimulation coding parameter.

Figure 7:
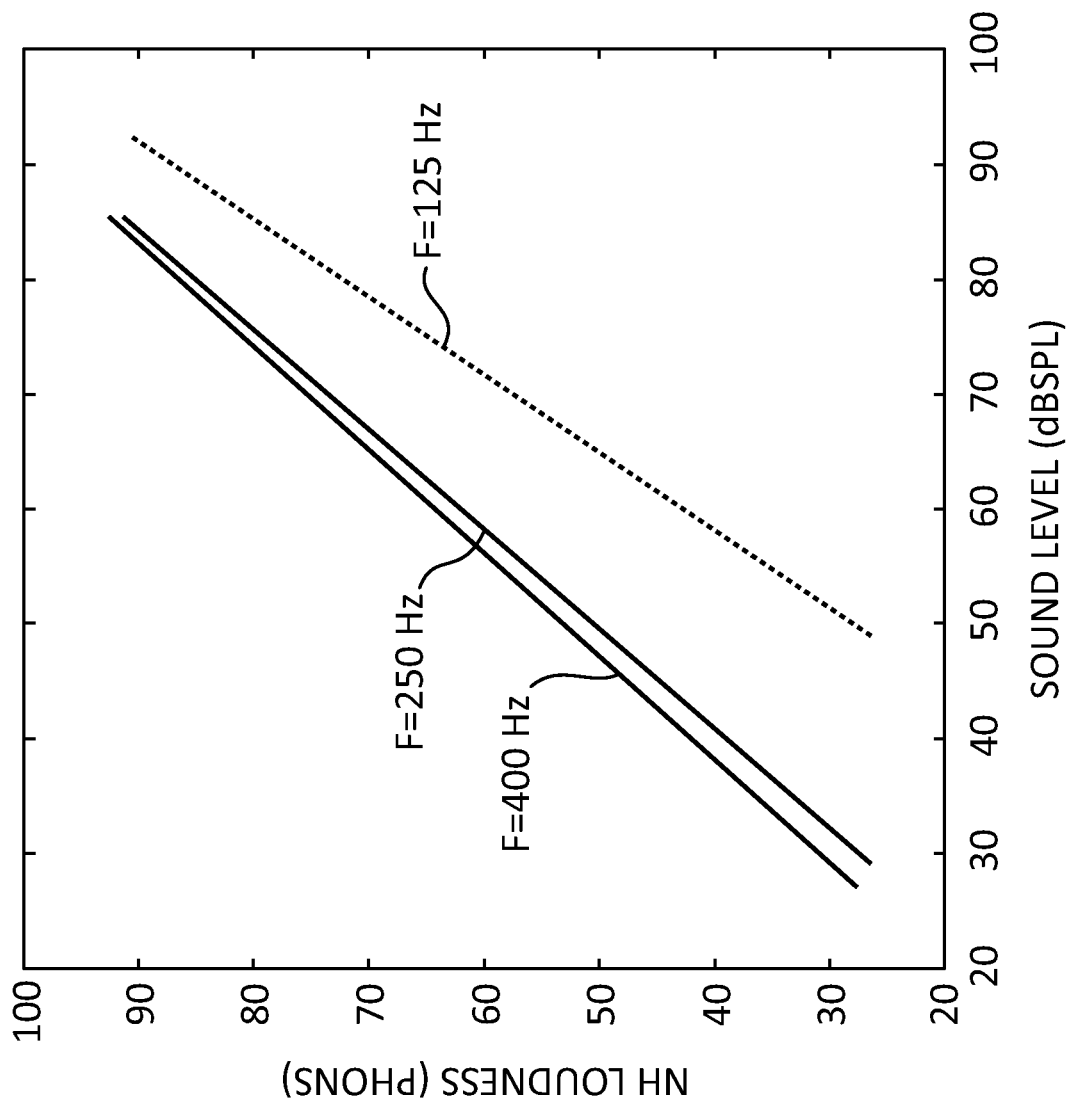
FIG. 7 illustrates a normal hearing loudness as a function of sound levels.

FIG. 7 illustrates an example of a relation between normal hearing loudness and sound levels for different frequencies. The loudness growth is seen as being linearly for normal hearing and the same loudness growth is being transformed to a secondary hearing loudness. The transformation from the normal hearing loudness to a secondary hearing loudness may be done linearly without affecting temporal fine components of the audio.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, elements, components, and/or steps but do not preclude the presence or addition of one or more other features, elements, components, and/or steps thereof. It will also be understood that when an element is referred to as being "connected" or "coupled" to another element, it can be directly connected or coupled to the other element, but an intervening element may also be present, unless expressly stated otherwise. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The scope should be judged in terms of the claims that follow.

The invention claimed is:

1. A method for providing one or more stimulation coding parameters in a hearing aid system for obtaining a perceivable secondary hearing loudness, comprising;
    receiving an acoustical input and providing an audio signal based on the acoustical input, and wherein the audio signal includes a sound pressure level at a frequency within a frequency range of between 10 Hz and 12 KHz;
    determining a normal hearing loudness at the frequency and at the sound pressure level via a normal hearing loudness model, where the normal hearing loudness model includes a plurality of normal hearing loudness as a function of a plurality of sound pressure levels and for one or more frequencies;
    transforming the normal hearing loudness to a secondary hearing loudness at the frequency based on a loudness scheme, and where the loudness scheme includes a relation between a plurality of normal hearing loudness and a plurality of secondary hearing loudness;
    determining a stimulation level at the frequency having the secondary hearing loudness within a dynamic range of a recipient of the hearing aid system based on the secondary hearing loudness and a stimulation model, where the stimulation model includes a relation between a plurality of stimulation levels and a plurality of secondary hearing loudness;
    determining one or more stimulation coding parameters for the frequency and based on a coding parameter model, where the coding parameter model includes a relation between the determined stimulation level and the one or more stimulation coding parameters for one or more frequencies; and
    generating audible stimulations based on the one or more stimulation coding parameters and providing the audible stimulations via a sound output unit of the hearing aid system to auditory nerve fibers of the recipient of the hearing aid system.

2. The method according to claim 1, wherein the loudness scheme includes;
    a first relation between a plurality of normal hearing loudness perceived by a normal-hearing person and a plurality of secondary hearing loudness perceived by a hearing-impaired person, where the first relation is equate resulting in a primary slope, or
    a second relation between a plurality of normal hearing loudness perceived by a normal-hearing person and a plurality of secondary hearing loudness perceived by a hearing-impaired person, where the second relation includes a secondary first slope and a secondary second slope, and where the secondary first slope is larger then the secondary second slope.

3. The method according to claim 2, wherein the stimulation model is determined based on following equation for the frequency;

$$SL = \frac{1}{1 + e^{-a(2HL-c)}},$$

where SL is the stimulation level, 2HL is the secondary hearing loudness, a and c are fitting parameters.

4. The method according to claim 2, wherein the coding parameter model is determined based on following equation;

$$SCP = e^{\left(SL \cdot \log\left(\frac{X_C}{X_T}\right) + \log(X_T)\right)},$$

where SL is stimulation level, SCP is one of the one or more stimulation coding parameters, $X_T$ is a first coding parameter threshold at a hearing threshold level (T-level) predetermined for the recipient, $X_c$ is a second coding parameter threshold at a hearing comfortable level (C-level) predetermined for the recipient, and where x, $X_T$, and $X_c$ are the same coding parameter type.

5. The method according to claim 2, wherein the hearing aid system is a cochlear implant system, a bone conduction hearing aid or a normal hearing aid not being a cochlear implant system or a bone conduction hearing aid.

6. The method according to claim 1, wherein the stimulation model is determined based on following equation for the frequency;

$$SL = \frac{1}{1 + e^{-a(2HL-c)}},$$

where SL is the stimulation level, 2HL is the secondary hearing loudness, a and c are fitting parameters.

7. The method according to claim 6, wherein the coding parameter model is determined based on following equation;

$$SCP = e^{\left(SL \cdot \log\left(\frac{X_C}{X_T}\right) + \log(X_T)\right)},$$

where SL is stimulation level, SCP is one of the one or more stimulation coding parameters, $X_T$ is a first coding parameter threshold at a hearing threshold level (T-level) predetermined for the recipient, $X_c$ is a second coding parameter threshold at a hearing comfortable level (C-level) predetermined for the recipient, and where x, $X_T$, and $X_c$ are the same coding parameter type.

8. The method according to claim 6, wherein the hearing aid system is a cochlear implant system, a bone conduction hearing aid or a normal hearing aid not being a cochlear implant system or a bone conduction hearing aid.

9. The method according to claim 6, wherein the fitting parameters are determined based on a sigmoid function fitting of a relation between a plurality of stimulation levels and a plurality of secondary hearing loudness of multiple other users or of the recipient.

10. The method according to claim 9, wherein the coding parameter model is determined based on following equation;

$$SCP = e^{\left(SL \cdot \log\left(\frac{X_C}{X_T}\right) + \log(X_T)\right)},$$

where SL is stimulation level, SCP is one of the one or more stimulation coding parameters, $X_T$ is a first coding parameter threshold at a hearing threshold level (T-level) predetermined for the recipient, $X_c$ is a second coding parameter threshold at a hearing comfortable level (C-level) predetermined for the recipient, and where x, $X_T$, and $X_c$ are the same coding parameter type.

11. The method according to claim 9, wherein the hearing aid system is a cochlear implant system, a bone conduction hearing aid or a normal hearing aid not being a cochlear implant system or a bone conduction hearing aid.

12. The method according to claim 1, wherein the coding parameter model is determined based on following equation;

$$SCP = e^{\left(SL \cdot \log\left(\frac{X_C}{X_T}\right) + \log(X_T)\right)},$$

where SL is stimulation level, SCP is one of the one or more stimulation coding parameters, $X_T$ is a first coding parameter threshold at a hearing threshold level (T-level) predetermined for the recipient, $X_c$ is a second coding parameter threshold at a hearing comfortable level (C-level) predetermined for the recipient, and where x, $X_T$, and $X_c$ are the same coding parameter type.

13. The method according to claim 1, wherein the hearing aid system is a cochlear implant system, a bone conduction hearing aid or a normal hearing aid not being a cochlear implant system or a bone conduction hearing aid.

14. The method according to claim 1, wherein the acoustical input is divided into a plurality of audio signals via a filter bank, and wherein the audio signal of the plurality of audio signals is band limited to a frequency range determined by a bandwidth and a centre frequency of a bandpass filter of the filter bank.

15. A hearing aid system comprising;
a microphone unit configured to receive an acoustical input and provide an audio signal based on the acoustical input, and wherein the audio signal includes a sound pressure level at a frequency within a frequency range of between 10 Hz and 12 KHz;
a storing unit including a normal hearing loudness model, a loudness scheme, a stimulation model and a coding parameter model;
a sound output unit configured to stimulate auditory nerve fibers of a recipient of the hearing aid system based on audible stimulations;
a processing unit configured to;
  determine a normal hearing loudness at the frequency and at the sound pressure level via the normal hearing loudness model, and the normal hearing loudness model includes a plurality of normal hearing loudness as a function of a plurality of sound pressure levels and for one or more frequencies;
  transform the normal hearing loudness to a secondary hearing loudness at the frequency based on a loudness scheme, and where the loudness scheme includes a relation between a plurality of normal hearing loudness and a plurality of secondary hearing loudness;
  determine a stimulation level at the frequency and within a dynamic range of a recipient of the hearing aid system based on the secondary hearing loudness and the stimulation model, where the stimulation model includes a relation between a plurality of stimulation levels and a plurality of secondary hearing loudness;
  determine one or more stimulation coding parameters at the frequency and based on the coding parameter model, where the coding parameter model includes a relation between the determined stimulation level and the one or more stimulation coding parameters; and
wherein the processing unit is configured to generate the audible stimulations based on the determined one or more stimulation coding parameters and provide the audible stimulations via the sound output unit to the auditory nerve fibers of the recipient of the hearing aid system.

16. A hearing aid system according to claim 15, wherein the loudness scheme includes;
a first relation between a plurality of normal hearing loudness perceived by a normal hearing person and a plurality of secondary hearing loudness perceived by a hearing impaired, where the first relation is equate resulting in a primary slope, and/or
a second relation between a plurality of normal hearing loudness perceived by a normal hearing person and a plurality of secondary hearing loudness perceived by a hearing impaired, where the second relation includes a secondary first slope and a secondary second slope, and where the secondary first slope is larger then the secondary second slope.

17. The hearing aid system according to claim 15, wherein the stimulation model is determined based on following equation;

$$SL = \frac{1}{1 + e^{-a(2HL-c)}},$$

where SL is the stimulation level, 2HL is a secondary hearing loudness, a and c are fitting parameters which is determined based on a frequency of the audio signal.

18. The hearing aid system according to claim 17, wherein the fitting parameters are determined based on a sigmoid function fitting of a relation between a plurality of stimulation levels and a plurality of secondary hearing loudness of multiple other users or of the recipient.

19. The hearing aid system according to claim 15, wherein the coding parameter model is determined based on following equation;

$$SCP = e^{\left(SL \cdot \log\left(\frac{X_C}{X_T}\right) + \log(X_T)\right)},$$

where SL is the stimulation level, SCP is one of the one or more stimulation coding parameters, $X_T$ is a first coding parameter threshold at a hearing threshold level (T-level) predetermined for the recipient, $X_c$ is a second coding parameter threshold at a hearing comfortable level (C-level) predetermined for the recipient, and where SCP, $X_T$, and $X_c$ are the same coding parameter type.

20. The hearing aid system according to claim 15, wherein the hearing aid system is a cochlear implant system, a bone conduction hearing aid or an acoustical hearing aid not being a cochlear implant or a bone conduction hearing aid.

\* \* \* \* \*